United States Patent
Ryabova et al.

(10) Patent No.: US 8,642,784 B2
(45) Date of Patent: Feb. 4, 2014

(54) BIOLOGICALLY ACTIVE COMPOUND N-[3-(4-NITROPHENYLAMINO)-INDOLE-2-ILMETHYLENE]AMINOGUANIDINE HYDROCHLORIDE WITH ANTI-INFLAMMATORY ACTIVITY

(75) Inventors: Svetlana Yurevna Ryabova, Moscow (RU); Valery Aleksandrovich Parshin, Moscow (RU); Marina Alekseevna Kalinkina, Moscow (RU); Vladimir Grigorevich Granik, Moscow (RU); Vladimir Vladimirovich Granik, legal representative, Moscow (RU); Nikita Borisovich Grigoriev, Moscow (RU); Viktoriya Isaakovna Levina, Moscow (RU); Elena Konstantinovna Panisheva, Moscow (RU); Sergey Anatolevich Zaycev, Mytischi (RU)

(73) Assignee: Obschestvo S Ogranichennoy Otvetstvennostyu "Polyar" (OOO Polyar), Tomsk (RU)

( * ) Notice: Subject to any disclaimer, the term of this patent is extended or adjusted under 35 U.S.C. 154(b) by 0 days.

(21) Appl. No.: 13/634,840

(22) PCT Filed: Mar. 11, 2011

(86) PCT No.: PCT/RU2011/000142
§ 371 (c)(1),
(2), (4) Date: Sep. 13, 2012

(87) PCT Pub. No.: WO2011/115527
PCT Pub. Date: Sep. 22, 2011

(65) Prior Publication Data
US 2013/0012724 A1 Jan. 10, 2013

(30) Foreign Application Priority Data
Mar. 15, 2010 (RU) ................. 2010109357

(51) Int. Cl.
C07D 209/40 (2006.01)
(52) U.S. Cl.
USPC ........................................ 548/483
(58) Field of Classification Search
USPC ........................................ 548/483
See application file for complete search history.

(56) References Cited

U.S. PATENT DOCUMENTS 6,063,807 A 5/2000 Chabrier de Lassauniere et al.

FOREIGN PATENT DOCUMENTS

| RU | 2095347 | 11/1997 |
| RU | 2167856 | 5/2001 |

OTHER PUBLICATIONS

Mashkovsky M.D. // Medical drugs, ed.13, Kharkov, Torgsyn, 1997.
Saavedra J.E., Billiar T.R., Williams D.L., et al. // J. Med. Chem. 1997, 40, 1947.
Granik V.G., Grigoriev N. B. // Nitric oxide, Moscow, Vuzovskaya Kniga, 2004.
Schwarz G.I., Syubaev R.D. / Шварц Г.Я., Сюбаев Р.Д. / Methodical recommendations on experimental (preclinical) research of new nonsteroidal anti-inflammatory drugs // News of Scientific Center of Examination and State Control LS MZ of Russia, 2000, No. 1, p. 44-50.
Cuzzocrea S., Mazzon E., Dugo L., et al. / Protective effects of n-acetylcysteine on lung injury and red blood cell modification induced by carrageenan in the rat // FASEB J., 2001, 15(7), p. 1187-1200.
Freyria AM, Paul J., Belleville J., et al. / Rat peritoneal macrophage procoagulant and fibrinolytic activities. An expression of the local inflammatory response // Comp. Biochem. Physiol. A. 1991, V99, N4, p. 517-524.
Vogel H.G. // Drug Discovery and evaluation: Pharmacological assays. Springer, 2008.
Ryabova S.Y., Tugusheva N.Z., Alexeeva L.M., Granik V.G. // Chem. Pharm. Journal, 1996, v.30, No. 7, p. 42-46.
Ryabova S.Y., Rastorgueva N.A., Lisitsa E.A., et al. // Academy of Sciences News, Ser. Chem., 2003, No. 6, p. 1312-1323.
Garuti, L Ricerche su sostanze ad attivita antivirale. Nota XVIII. Bis-amidinoidrazoni di dialdeidi aromatiche N-eterocicliche. II Farmaco, Edizione Scientifica, 1981, 36(6), pp. 393-399.
Written Opinion of the International Searching Authority dated Aug. 11, 2011, in corresponding Russian patent application No. PCT/RU2011/000142.

*Primary Examiner* — Shawquia Young
(74) *Attorney, Agent, or Firm* — Dergosits & Noah LLP

(57) ABSTRACT

The present invention relates to chemical-pharmaceutical industry and medicine. The present invention relates to N-[3-(4-nitrophenylamino)-indole-2-ilmethylene]aminoguanidine hydrochloride of formula (2) having anti-inflammatory and chondroprotective activity. The compound does not exhibit adverse effects.

3 Claims, No Drawings

BIOLOGICALLY ACTIVE COMPOUND N-[3-(4-NITROPHENYLAMINO)-INDOLE-2-ILMETHYLENE]AMINOGUANIDINE HYDROCHLORIDE WITH ANTI-INFLAMMATORY ACTIVITY

CROSS REFERENCE TO RELATED APPLICATION

This application is a U.S. National Phase of International Application No. PCT/RU2011/000142 filed on Mar. 11, 2011, which claims priority to and the benefit of Russian Patent Application No. 2010109357 filed on Mar. 15, 2010, the entire contents of which are incorporated herein by reference.

FIELD OF THE INVENTION

This invention concerns chemical-pharmaceutical industry and relates to a new compound that can be used as an anti-inflammatory drug.

BACKGROUND OF THE INVENTION

It is well known that nonsteroidal anti-inflammatory drugs (NSAIDs) like acetylsalicylic acid, indomethacin, voltaren (sodium diclofenac), ibuprofen (brufen) and others are the most widely used drugs for treating inflammatory pathology [1]. The main adverse effect of NSAIDs is their ulcerogenic action (the ability to damage gastric and duodenal mucous membranes, possibly causing ulcer diseases) due to their effect on prostaglandin synthesis—NSAIDs inhibit biological synthesis of prostaglandins that are physiologic (endogenous) gastric cytoprotectants.

This makes the research of new compounds, having systemic anti-inflammatory effect but lacking ulcerogenic effects, quite important.

A promising venue of such research would be the development of a compound having significant anti-inflammatory effect which is not related to the inhibition of prostaglandin synthesis, but acts on the organism via different mechanism of action.

It is well known that some guanidine derivatives are markedly antagonistic towards nitric oxide (NO) synthases. Especially noteworthy among them are N-aminoguanidine (1) [2], and some of its derivatives.

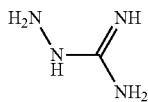

In most in vitro systems aminoguanidine and a known NO-synthase inhibitor L-NMMA (NG-monomethyl-L-arginine) are equally effective in inhibiting inducible isoenzymes, but the former is much less active towards constitutive forms, i.e. the former is much more selective [3].

In animal models aminoguanidine reduces the severity of inflammation and septic shock, improves survival during endotoxin administration.

In treating inflammatory diseases aminoguanidine activity profile is favorable for the patient.

A closest analog of aminoguanidine are salts of amidine derivatives and of cyclooxygenase (COX) inhibitor of a general formula AB, in which A—COX inhibitor with carboxylic function; B— a compound of general formula

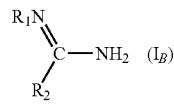

Compounds provided by the invention [8] possess double biological effect—they inhibit NO synthesis and COX activity and can be used as anti-inflammatory compounds. However they also have, to a lesser degree, adverse effects present in aforementioned NSAIDs.

SUMMARY OF THE INVENTION

The goal of the present invention is the development of a new anti-inflammatory drug that does not have ulcerogenic effects.

To achieve this it was deemed necessary to develop a compound that would not only have an aminoguanidine fragment in its structure, but could also metabolize in the organism, releasing aminoguanidine.

The present invention provides a compound with such properties —N-[3-(4-nitrophenylamino)-indole-2-ilmethylene]aminoguanidine hydrochloride of a formula (2):

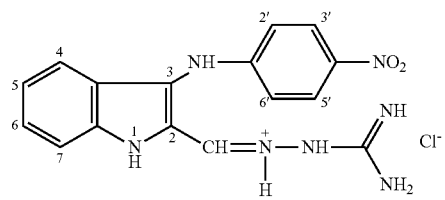

The presence of imine structure gives the compound a property to hydrolyze (like all imines) in aqueous medium (scheme 1), generating 2-formyl-3-p-nitrophenylindiol (3) and aminoguanidine hydrochloride:

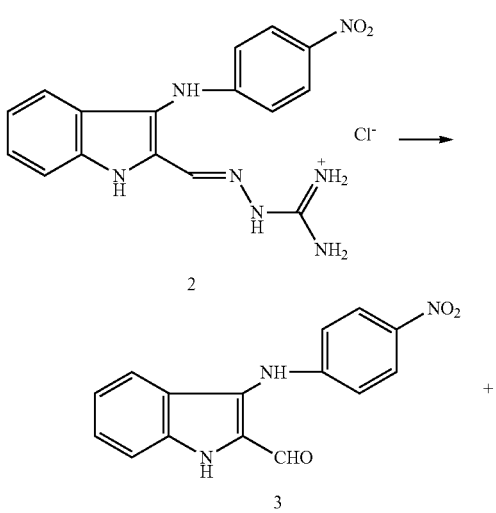

-continued

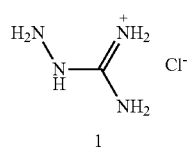

DETAILED DESCRIPTION OF THE PRESENT INVENTION

The present invention provides a method of synthesizing N-[3-(4-nitrophenylamino)-indole-2-ilmethylene]aminoguanidine hydrochloride of a formula (2), based on the interaction of 2-formyl-3-(4-nitrophenyl)aminoindole [9,10] and aminoguanidine catalyzed by hydrochloric acid while heating the mixture in rectified alcohol, ensuring technologically acceptable conditions of synthesizing the target product from readily available raw materials and without the need for special technological conditions.

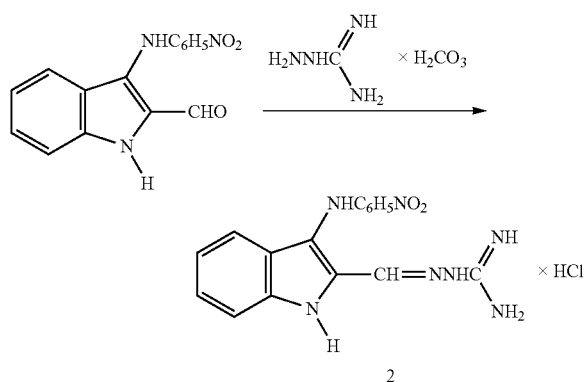

The new compound has important pharmacological properties: it possesses systemic anti-inflammatory effect and has chondroprotective properties.

The possibility of implementation of the present invention can be demonstrated by the following examples:

Example 1

Synthesis of N-[3-(4-nitrophenylamino)-indole-2-ilmethylene]aminoguanidine hydrochloride (2)

A mixture of 1 g (0.356 μmol) of 2-formyl-3-(4-nitrophenyl)aminoindole, 0.58 g (0.45 μmol) of aminoguanidine carbonate, 0.87 ml (0.86 μmol) of concentrated hydrochloric acid, 0.87 ml of water and 26 ml of rectified ethanol is boiled for 1.5 hours. It is then cooled, the residue is filtered, rinsed by alcohol and acetone. 1.23 g of hydrochloride is obtained, which is then re-crystallized in a mixture of ethanol and water (3:1). Yield 0.8 g (65%). Melting point 310-312° C.

In big loads the substance was crystallized from aqueous N,N-dimethylfomamide (DMFA).

The obtained compound has the following NMR-spectrum parameters:

$^1$H NMR(DMS-$d_6$, δ): 6.75 and 8.03
7.02, 7.26, 7.44, (all m. 1H, 2H, 1H, 4H, 7H)
7.83 (br.s, 4H, HN—CH=NH$_2$)
8.18 (s. 1H-α-H)
9.21, 11.69, 11.98 (br.s, 1H, NH(Ph), NH (indole), NH$^+$)

Example 2

Study of the Compound's Toxicity

Study of the compound of formula 2 was conducted in vivo. The most effective NSAIDs—voltaren and indomethacin were chosen as drugs of comparison, their main drawback is the aforementioned ulcerogenic action. To determine the doses of the compound that would need to be studied, it is first necessary to study its toxicity. Studies were carried out in male mice with body mass 18-20 g. Compound 2 was administered as a water suspension. Each dose was administered to 5 animals. Behavior and overall condition of animals were observed during 5 days. LD$_{50}$ (the dose causing the death of 50% of animals) was calculated using Karber method.

TABLE 1

The effect of the studied compound on mice mortality

| Dose, mg/kg intravenous | Number of animals in a group | Animal mortality | | Note |
|---|---|---|---|---|
| | | Alive | Dead | |
| 500.0 | 5 | 5 | 0 | Normal behavior |
| 1000.0 | 5 | 5 | 0 | Normal behavior |
| 1500.0 | 5 | 5 | 0 | Normal behavior |
| 2000.0 | 5 | 4 | 1 | Animals depressed |

Because only one animal of five died after intravenous administration of the compound in 2000.0 mg/kg, we can claim that the studied compound belongs to the third class of danger, as specified by GOST 12.1.007-76 (classification of harmful industrial substances)—moderately dangerous substance. Because LD$_{50}$ in oral administration may exceed 5000 mg/kg, the compound of formula 2 may be rated as 4 class—low-danger substances, i.e. the compound is almost non-toxic.

Example 3

Study of Anti-Inflammatory Activity

Activity was studies using the methods listed in "Methodical recommendations on experimental (preclinical) research of new nonsteroidal anti-inflammatory drugs" for new compounds screening, in animal models of peritonitis induced by lipopolysaccharide (LPS) and carrageenan [4].

1. Carrageenan-Induced Peritonitis in Mice

Research was carried out by a method described in [5]. Experiments were performed using male mice with body mass 23-24 g, in groups of 10 animals. The studied compounds were administered by a tube into the stomach 1.5 hours before intraperitoneal administration of 0.2 ml 1% γ-carrageenan, after 4 hours the animals were sacrificed and the volume of exudate in peritoneal cavity was measured in ml. The results were processed using variation statistics methods for biological research (mean standard error, means were calculated using Student's t-distribution).

2. LPS-induced Peritonitis in Mice

Anti-exudative action was studied in male mice with body mice 22.0-23.0 g. Peritonitis was induced by intraperitoneal administration of lipopolysaccharide (LPS), produced from *Escherichia coli* (Sigma) 1.0 mg/kg, as described in [6]: after 4 hours the animals were sacrificed by CO$_2$, their peritoneal cavity opened and the volume of exudate was measured in ml. Studied compounds and drugs of comparison were administered per os one hour before LPS, control group was composed of mice receiving 0.3 ml of saline before LPS administration. Each group had 10 animals.

The results were processed using variation statistics methods for biological research (mean standard error, means were calculated using Student's t-distribution).

Results of the Study

Results of experiments and assessment of anti-inflammatory activity of compound 2 are shown in table 2.

TABLE 2

Anti-inflammatory activity of compound 2 in mice peritonitis models.

| Studied compounds | Dose, mg/kg (per os) | Number of animals in the group | Anti-inflammatory activity in carrageenan-induced peritonitis model, % of control | Anti-inflammatory activity in LPS-induced peritonitis model, % of control |
|---|---|---|---|---|
| Compound of formula 2 | 25.0 | 10 | 3.9 | 2.2 |
|  | 50.0 | 10 | 21.6* | 46.7* |
|  | 100.0 | 10 | 45.1* | 88.9* |
|  | 200.0 | 10 | 84.3* | 100.0* |
| Voltaren | 25.0 | 10 | 80.4* | 82.2* |
|  | 50.0 | 10 | 90.2* | 95.6* |
|  | 100.0 | 10 | 100.0* | 100.0* |
| Aminoguanidine | 50.0 | 10 | 25.5* | 51.1* |
|  | 100.0 | 10 | 70.6* | 73.3* |
|  | 200.0 | 10 | 84.3* | 91.1* |

*$p < 0.05$ compared to control

LPS-induced Peritonitis in Rats.

Anti-exudative action was studied in male rate with body mass 170.0-180.0 g. Peritonitis was induced by intraperitoneal administration of lipopolysaccharide (LPS), produced from *Escherichia coli* (Sigma)—1.0 mg/kg as described in [6]: after 4 hours the animals were sacrificed by $CO_2$, their peritoneal cavity opened and the volume of exudate was measured in ml. Studied compounds and drugs of comparison were administered per os one hour before LPS, control group was composed of rats receiving 0.3 ml of saline before LPS administration. Each group had 7 animals.

The results were processed using variation statistics methods for biological research (mean standard error, means were calculated using Student's t-distribution).

Results of the Study

Assessment of anti-inflammatory activity of compound 2 compared to voltaren and aminoguanidine is shown in table 3.

TABLE 3

Anti-inflammatory activity of compound 2 in rat peritonitis models.

| Studied compounds | Dose, mg/kg (per os) | Number of animals in the group | Anti-inflammatory activity in LPS-induced peritonitis model, % of control | $ED_{50}$, mg/kg |
|---|---|---|---|---|
| Compound of formula 2 | 10.0 | 7 | 2.0 | 48.0 ± 4.5 |
|  | 25.0 | 7 | 26.0* |  |
|  | 50.0 | 7 | 58.0* |  |
|  | 75.0 | 7 | 78.0* |  |
|  | 100.0 | 7 | 100.0* |  |
| Voltaren | 10.0 | 7 | 22.0 | 20.0 ± 1.5 |
|  | 25.0 | 7 | 65.0* |  |
|  | 50.0 | 7 | 84.0* |  |
|  | 75.0 | 7 | 100.0* |  |
| Aminoguanidine | 25.0 | 7 | 4.0 | 70.0 ± 2.5 |
|  | 50.0 | 7 | 22.0* |  |
|  | 75.0 | 7 | 58.0* |  |
|  | 100.0 | 7 | 78.0* |  |
|  | 200.0 | 7 | 100.0* |  |

*$p < 0.05$ compared to control

Anti-inflammatory activity of compound of formula 2 was studied. Results, shown in tables 2 and 3 indicate that the described potential drug of formula 2 is somewhat inferior to voltaren in used models, but is better than aminoguanidine.

Compound 2 exhibits anti-inflammatory action. Most NSAIDs frequently have adverse effects—damage of gastric mucous membranes and ulcerogenic effect, so the study of ulcerogenic effects of potential NSAIDs allows to detect the presence and severity of ulcerogenic effects and to approximate the effect of the studied compound on prostaglandin synthesis.

Methods of the Study

Ulcerogenic effect of compound 2 was studied in accordance with Methodical recommendations on experimental (preclinical) research of new nonsteroidal anti-inflammatory drugs [4]. Studies were performed according to the following scheme:
1. Study of the compounds' irritant action on mice stomach using doses five-times higher than pharmacological dose (single administration).
2. Study of the compounds' ulcerogenic action using pharmaceutical dose during 7 days of administration.
3. Aggravation of ulcerogenic effects of studied compounds by 0.6H hydrochloric acid.
4. Aggravation of ulcerogenic effects of studied compounds by the known NSAIDs (indomethacin).
1. Study of Irritant Action of Compound 2

Male mice with body mass 23-24 g were deprived of food for 24 hours, water access was not limited. Number of animals in a group-10.

Compound 2 in 500 mg/kg dose was administered by a tube into the stomach, after 6 hours the animals were sacrificed, their stomachs extracted, number of ulcers counted and ulcerogenic index calculated. Ulcerogenic effect was assessed using 4-point scale: 0—no damage; 0.5—hyperemia; 1—insignificant damage (1 or 2 small bleedings); 2—multiple damage (erosions, small bleedings); 3—significant and multiple damage (erosions, bleedings); 4—severe damage, affecting all gastric mucosa (massive bleedings, erosions, perforations).
2. Study of Irritant Action of Compound 2.

Male mice with body mass 23-24 g were administered compound 2 in 200 mg/kg dose per os for 7 days. After 7 days the animals were sacrificed by $CO_2$, their stomachs extracted and the number of ulcers counted.

Drugs of comparison: indomethacin 20 mg/kg, voltaren— 50 mg/kg and aminoguanidine—200 mg/kg. Each test group had 10 animals.
3. Aggravation of Ulcerogenic Effects of Studied Compounds by 0.6H Hydrochloric Acid.

Male mice with body mass 23-24 g were deprived of food for 24 hours, water access was not limited. Compound 2 in 100 mg/kg dose was administered by a tube into the stomach 1 hour before the administration of 0.6H hydrochloric acid (5 ml/kg), after 4 hours the animals were sacrificed, their stomachs extracted and the number of ulcers counted.

Drugs of comparison: indomethacin 20 mg/kg, voltaren—50 mg/kg and aminoguanidine—200 mg/kg. Each test group had 10 animals.

4. Aggravation of Ulcerogenic Effect of Compound 2 by the Known Nonsteroidal Anti-Inflammatory Drugs [1,4].

Male mice with body mass 23-24 g were deprived of food for 24 hours, water access was not limited. Compound 2 in 100 mg/kg dose was administered by a tube into the stomach 1 hour before the administration of indomethacin (20 mg/kg), after 5 hours the animals were sacrificed, their stomachs extracted and the number of ulcers counted.

Drugs of comparison: voltaren—50 mg/kg and aminoguanidine—200 mg/kg. Each test group had 10 animals.

Results.

Results of study of ulcerogenic action of compound 2 compared to voltaren, indomethocine and aminoguanidine are shown in table 4.

Reduction of cartilage width in groups taking various concentrations of the new drug compared to control group was proven; chondroprotective effect of compound 2 was noted in 50 mg/kg dose.

Based on the aforementioned experimental research a conclusion was made that the new compound possesses systematic anti-inflammatory activity (reduces leukocytosis and pro-inflammatory TNFα cytokine synthesis) in intragastric administration (analog of per os). The studied compound in 50 and 75 mg/kg doses reduced the severity of hind leg swelling, in 50 mg/kg dose partially prevented the degeneration of articular carriage of hock. In the same dose the compound has shown a potent (better than indomethacin) chondroprotective action towards interphalangeal joints of affected leg (x-ray (röntgenography) data). In intragastric administration (analog of per os) the compound has shown systemic anti-inflammatory action (reduction of swelling, leukocytosis, TNFα level, chondroprotective action) that may be associated with the inhibition of delayed type hypersensitivity.

Assessment of other types of pharmaceutical activity of compound 2 has shown that the compound possesses anti-

TABLE 4

Ulcerogenic effects of studied compounds in different conditions

| Studied compounds | Average ulcerogenic index (4-point scale) of single administration of the compounds in 500.0 mg/kg dose | Average ulcerogenic index (4-point scale) of chronic administration of pharmacological dose | Average ulcerogenic index (4-point scale) of combining the studied compounds with indomethacin | Average ulcerogenic index (4-point scale) of combining the studied compounds with hydrochloric acid |
|---|---|---|---|---|
| 2 | 0 | 0 | 2.2 | 0.15 |
| Aminoguanidine | — | 0 | 0.19 | 0.15 |
| Voltaren | — | 0.35 | 2.5 | 0.55 |
| Indomethacin | — | 1.15 | — | 2.4 |
| Control | — | — | 2.0 | 0.2 |

*p < 0.05 compared to control

As the results show, compound of formula 2 does not have irritant effect on gastric mucosa both in single administration of 500 mg/kg dose and chronic use of 200 mg/kg doses. It also does not aggravate ulceration when combined with 0.6H hydrochloric acid or indomethacin in 20 mg/kg dose. Drugs of comparison voltaren and indomethacin had ulcerogenic effects, characteristic of NSAIDs.

Possible ulcerogenic action of compound 2 was thus studied, and it was proven that, like aminoguanidine and in contrast to voltaren and indomethacin, compound 2 does not exhibit irritant and ulcerogenic effects in several ulceration models.

Example 4

Study of Chondroprotective Properties

Compound of formula 2 was tested in chronic arthritis (adjuvant arthritis) model in Wistar rats. It was shown that the studied compound has prevented the spreading of inflammation, reducing leukocytosis, tumor necrosis factor-alpha (TNFα) in blood plasma and inhibiting the development of delayed type hypersensitivity (according to the data of x-ray (rontgenographic) study of interphalangeal joints of affected hind leg). The compound in 50 mg/kg dose reduced the level of TNFα as good as the drug of comparison—indomethacin. Compound 2 in 50 mg/kg dose was most effective in inhibiting the development of joint sclerosis and degradation of hind leg interphalangeal joints, better than the drug of comparison.

allergic, antihypoxic and analgesic activity. All discovered types of pharmacological activity of compound 2 are present not only in its hydrochloride form, but also in its other pharmaceutically acceptable salts (e.g. Na, K, Ca, Mg), and also in complex combinations with pharmaceutically acceptable complexones (e.g. with glycyrrhizic acid).

REFERENCES

1. Mashkovsky M. D.//Medical drugs, ed.13, Kharkov, Torgsyn, 1997.
2. Saavedra J. E., Billiar T. R., Williams D. L., et al.//J. Med. Chem. 1997, 40, 1947.
3. Granik V. G., Grigoriev N. B.//Nitric oxide, Moscow, Vuzovskaya Kniga, 2004.
4. Schwarz G. I., Syubaev R. D./ Шварц Г.Я Сюбаев Р.Д/Methodical recommendations on experimental (preclinical) research of new nonsteroidal anti-inflammatory drugs//News of Scientific Center of Examination and State Control LS MZ of Russia, 2000, No 1, P. 44-50.
3. Cuzzocrea S., Mazzon E., Dugo L., et al./Protective effects of n-acetylcysteine on lung injury and red blood cell modification induced by carrageenan in the rat//FASEB J., 2001, 15(7), P. 1187-1200.
4. Freyria A M, Paul J., Belleville J., et al./Rat peritoneal macrophage procoagulant and fibrinolytic activities. An expression of the local inflammatory response//Comp. Biochem. Physiol. A. 1991, V99, N4, P.517-524.

5. Vogel H. G.//Drug Discovery and evaluation: Pharmacological assays. Springer, 2008.
6. Russian patent RU 2167856.
7. Ryabova S. Y., Tugusheva N. Z., Alexeeva L. M., Granik V. G.//Chem. Pharm. Journal, 1996, v.30, No 7, P. 42-46.
8. Ryabova S. Y., Rastorgueva N. A., Lisitsa E. A., et al.// Academy of Sciences News, Ser. Chem., 2003, No. 6, P. 1312-1323.

The invention claimed is:

1. N-[3-(4-nitrophenylamino)-indole-2-ilmethylene]aminoguanidine hydrochloride of formula (2)

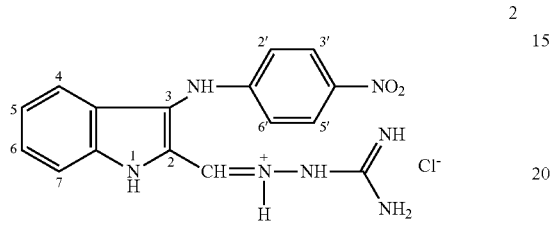

or its pharmaceutically acceptable salt.

2. N-[3-(4-nitrophenylamino)-indole-2-ilmethylene]aminoguanidine hydrochloride of formula (2) according to claim 1, having systemic anti-inflammatory action.

3. N-[3-(4-nitrophenylamino)-indole-2-ilmethylene]aminoguanidine hydrochloride of formula (2) according to claim 1, having chondroprotective action.

* * * * *